(12) United States Patent
Le et al.

(10) Patent No.: US 6,355,027 B1
(45) Date of Patent: Mar. 12, 2002

(54) FLEXIBLE MICROCATHETER

(75) Inventors: Hieu V. Le; John Edward Morris, both of Minneapolis; Cindy M. Setum, Plymouth; Robert G. Dutcher, Maple Grove, all of MN (US)

(73) Assignee: Possis Medical, Inc., Minneapolis, MN (US)

(*) Notice: Subject to any disclaimer, the term of this patent is extended or adjusted under 35 U.S.C. 154(b) by 0 days.

(21) Appl. No.: 09/328,761

(22) Filed: Jun. 9, 1999

(51) Int. Cl.[7] .............................................. A61M 25/00
(52) U.S. Cl. ...................................... 604/525; 604/526
(58) Field of Search ................................ 604/523, 524, 604/525, 526, 527, 529, 533, 264, 265, 93.01, 48

(56) References Cited

U.S. PATENT DOCUMENTS

| | | |
|---|---|---|
| 3,752,617 A | 8/1973 | Burlis et al. |
| 4,636,346 A | 1/1987 | Gold et al. |
| 4,739,768 A | 4/1988 | Engelson |
| 4,782,834 A | 11/1988 | Maguire et al. |
| 4,888,146 A | 12/1989 | Dandeneau |
| 4,898,591 A * | 2/1990 | Jang et al. ................... 604/282 |
| 5,085,649 A | 2/1992 | Flynn |
| 5,163,431 A | 11/1992 | Griep |
| 5,254,107 A | 10/1993 | Soltesz |
| 5,308,342 A | 5/1994 | Sepetka et al. |
| 5,342,386 A | 8/1994 | Trotta |
| 5,399,164 A | 3/1995 | Snoke et al. |
| 5,456,674 A | 10/1995 | Bos et al. |
| 5,478,330 A | 12/1995 | Imran et al. |
| 5,496,294 A | 3/1996 | Hergenrother et al. |
| 5,499,973 A | 3/1996 | Saab |
| 5,531,685 A | 7/1996 | Hemmer et al. |
| 5,542,924 A | 8/1996 | Snoke et al. |
| 5,554,121 A | 9/1996 | Ainsworth et al. |
| 5,599,325 A * | 2/1997 | Ju et al. ....................... 604/282 |
| 5,624,397 A | 4/1997 | Snoke et al. |
| 5,658,263 A * | 8/1997 | Dang et al. .................. 604/280 |
| 5,662,622 A | 9/1997 | Gore et al. |
| 5,676,659 A * | 10/1997 | McGurk ...................... 604/282 |
| 5,704,926 A | 1/1998 | Sutton |
| 6,030,369 A * | 2/2000 | Engelson et al. ........... 604/264 |
| 6,045,547 A * | 4/2000 | Ren et al. .................... 604/525 |
| 6,189,978 B1 * | 2/2001 | Samson et al. ........... 604/96.01 |

* cited by examiner

Primary Examiner—Richard K. Seidel
Assistant Examiner—Jennifer J Maynard
(74) Attorney, Agent, or Firm—Hugh D. Jaeger

(57) ABSTRACT

Flexible microcatheter having regions of different flexibility integrally and strategically placed along and about the length of a one-piece composite catheter tube. Distally the flexible microcatheter exhibits pronounced flexibility with respect to locations or regions of flexibility located proximally for navigation along tortuous vascular paths. Different regions of flexibility are formed by applying resins of different Shore hardness readings either singularly or in combination along and about a braid which overlies an inner resin layer. The encapsulated braid provides resistance to kinking and bending of the flexible microcatheter as well as providing for torque transmission and pushability along the length of the flexible microcatheter.

11 Claims, 3 Drawing Sheets

FLEXIBLE MICROCATHETER

BACKGROUND OF THE INVENTION

1. Field of the Invention

The present invention pertains to a catheter, and more particularly, pertains to a flexible microcatheter having continuous variability of stiffness or flexibility along and about the length of the flexible catheter. Embedded flexible braid wires surrounded by layers of varied hardness flexible plastic allows flexibility in different degrees for tracking and navigating along a tortuous vascular or other path.

2. Description of the Prior Art

Prior art catheter devices for use in small and tortuous vascular paths required catheters of minimum profile while yet requiring a great degree of flexibility. A catheter of minimum profile often could be flexible to a fault in that the catheter would tend to kink in a tight radius path, thereby causing a lumen flow restriction or stoppage. Difficulty could also be encountered in advancing the catheter along a path or application of torque-transfer, as the minimum profile structure did not provide the structural integrity required for advancement or twisting without the tube bending or kinking at various points along the catheter length.

The present invention provides a flexible microcatheter which overcomes the problems of prior art devices.

SUMMARY OF THE INVENTION

The present invention, a flexible microcatheter, is fashioned, in part, by a one-piece composite catheter tube composed of several layers of plastic including a polyethylene or polyamide copolymer or fluoroplastic inner layer or polyether block amide, a stainless steel or other braid material aligned over and about the inner layer to provide kink resistance and to increase torque transfer, and an outer layer of two polyamide and polyether or polyurethane based materials along and about the braid material and the inner layer. The inner layer has a constant hardness or flexibility while the length of the outer layer is comprised of regions of continually varying or different hardness or flexibility as determined by the composition of resin used to fashion the regions of the outer layer. The regions included are the distal region, a mid region of continually varying hardness located proximally and adjacent to the distal region and a proximal region located adjacent to and proximal to the mid region. The distal region exhibits the greatest amount of flexibility followed by regions of increasingly lesser flexibility in each successively and proximally located region of flexibility.

According to one embodiment of the present invention there is provided a flexible microcatheter having a Luer adapter, a strain relief and a one-piece composite catheter tube extending therefrom. The one-piece tube is comprised of a flexible plastic inner layer of constant hardness, a braid aligned over and about and along the inner layer and a flexible plastic outer layer having regions of different or continually varying hardness aligned over, about and along the braid and the inner layer. Marker bands and a distally located tip are included distally on the one-piece composite catheter tube.

One significant aspect and feature of the present invention is a flexible microcatheter having a variable degree of flexibility along its length. There is a mid region of flexibility which is continually varying.

Another significant aspect and feature of the present invention is a flexible microcatheter having a one-piece composite catheter tube.

Yet another significant aspect and feature of the present invention is a flexible microcatheter which encapsulates a braid between an inner and outer plastic layer, and is resistant to kinking and ovalization with bending.

Still another significant aspect and feature of the present invention is a flexible microcatheter which allows torque transfer.

A further significant aspect and feature of the present invention is a flexible microcatheter having a relatively stiff proximal region for application of push force to the distal flexible region(s).

A still further significant aspect and feature of the present invention is being able to vary stiffness without varying the outer dimension.

Having thus described one embodiment of the present invention, it is the principal object hereof to provide a flexible microcatheter.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE PREFERRED EMBODIMENTS

Figure 1:
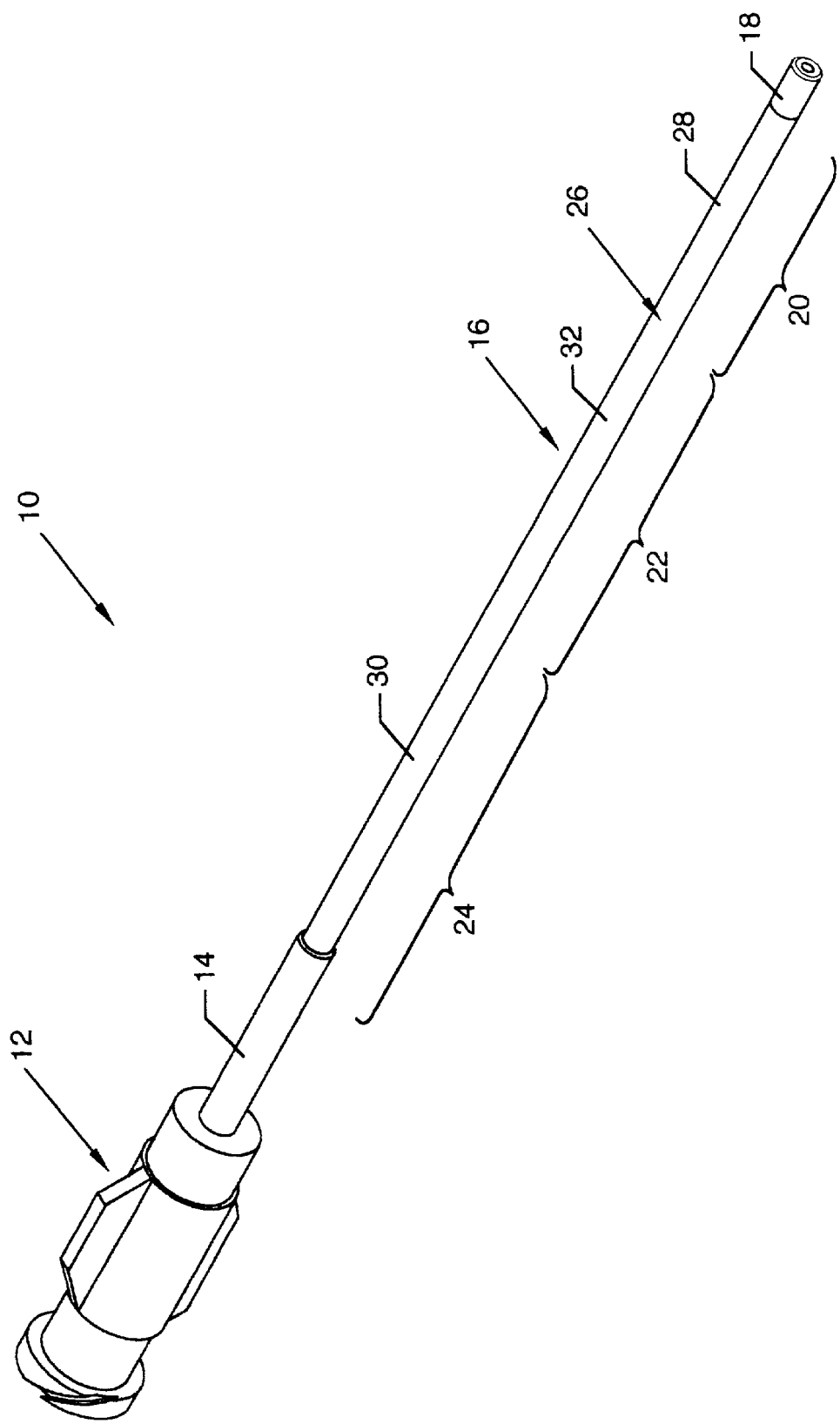
FIG. 1 illustrates an isometric view of a flexible microcatheter, the present invention.

FIG. 1 illustrates an isometric view of a flexible microcatheter 10, the present invention. Visible on the exterior of the flexible microcatheter 10 are a Luer connector 12, a strain relief 14 concentrically located with the Luer connector 12 and extending outwardly and distally therefrom, a one-piece composite catheter tube 16 extending through the strain relief 14 from the Luer connector 12, and a distally located atraumatic tip 18. Although not visible to the naked eye, the one-piece composite catheter tube 16 includes a distally located region of flexibility 20 juxtaposing the atraumatic tip 18, a mid region of flexibility 22 located proximal to the distally located region of flexibility 20, and a proximally located region of flexibility 24 located proximal to the mid region of flexibility 22. For purposes of example and illustration, the length of the one-piece composite catheter tube 16 measured from the strain relief to the atraumatic tip 18 can range from approximately 100 to 160 cm where the distal region of flexibility 20 can range from 10 to 30 cm, the mid region of flexibility 22 can range from 10 to 30 cm and the proximal region of flexibility 24 can range from 80 to 100 cm. Each region of flexibility, which is part and parcel of an outer layer 26, is formed in a continuous fashion which can be, but is not limited to, an extrusion process to provide composition of either one or another resin or a combination or mixture of resins over and about a braid and an inner layer (FIG. 2) to provide staged or graduated degrees or continuously variable degrees of flexibility according to a durometer reference. Through the extrusion process, an inner layer 34 and the outer layer 26 are thermally bonded. Application of one or more resins having different hardness or flexible qualities is a one step continuous application where resins are furnished and applied over the braid and the inner layer as a pure form or a mixed form to provide the proper hardness or flexibility. A single resin 28 having specific hardness qualities (25 D to 35 D) and which can be, but is not limited to, thermoplastics, polyether block amide, polyamide, polyurethane, or polyethylene, is applied over the braid and inner layer to form a part of the outer layer 26 designated as the distal region of flexibility 20 having, for purpose of example and illustration, a 25 D Shore hardness value within a Shore hardness range of 25 D to 63 D. Another single resin 30 which also can be, but is not limited to, thermoplastics, polyether block amide, polyamide, polyurethane, or polyethylene and having specific hardness qualities (70 D to 80 D) which are harder than the resin 28 and which is incorporated in the proximal region of flexibility 24, is then mixed as part of the continual process with resin 28 having lesser hardness qualities to form a combination resin 32, to be continually applied and bonded to and over the braid and inner layer to form a part of the outer layer 26 designated as the mid region of flexibility 22 having, for purpose of example and illustration, a middle range of 25 D to 75 D Shore hardness value. The mix of the combination resin 32 is changed during extrusion and is continuously variable to increase stiffness, or decrease flexibility, in a proximal direction to continuously and upwardly increase the Shore reading proximally. Single resin 30, as part of the continual application process, is applied over the braid and inner layer to form a part of the outer layer 26 designated as the proximal region of flexibility 24 having, for purpose of example and illustration, a 72 D Shore hardness value within a Shore hardness range of 50 D to 75 D. Although three regions of flexibility are described, any number of regions of flexibility can be utilized and shall not be limiting to the scope of the invention. The flexible microcatheter 10 which is provided is distally more flexible, which allows insertion of the atraumatic tip 18 and adjacent distal region of flexibility 20 into, and navigation of the balance of the flexible catheter structure along, tortuous vascular paths.

Figure 2:
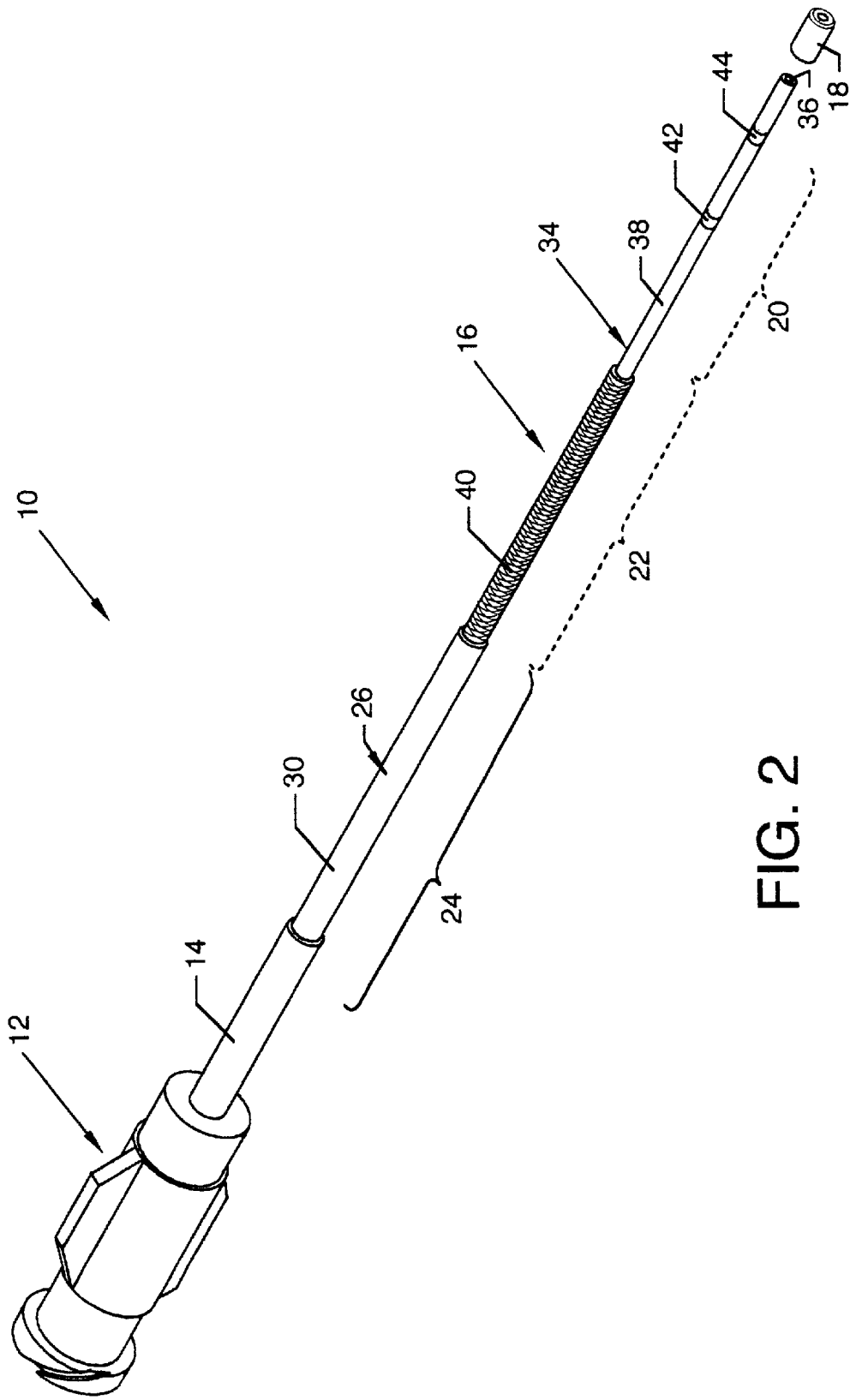
FIG. 2 illustrates a cutaway and partially exploded view of the flexible microcatheter; and, FIG. 3 illustrates a longitudinal cross sectional view of the flexible microcatheter.

FIG. 2 illustrates a cutaway and partially exploded view of the flexible microcatheter 10, where all numerals correspond to those elements previously or otherwise described. Central to the flexible microcatheter 10 is an inner layer 34 having a lumen 36. The inner layer 34 is formed over a mandrel or otherwise suitably formed from another single resin 38 having specific hardness qualities which can be, but is not limited to, thermoplastics, fluroplastics polyamide, polyethylene, or polyether block amide. The inner layer 34, for purposes of example and illustration, preferably can have a 50 D to 75 D Shore hardness value distributed constantly along its length, but in the alternative, can include regions of flexibility as required to provide various hardness or flexibility attributes. A braid 40 is aligned over and about the length of the inner layer 34 and extends from the atraumatic tip 18 to the interior of the Luer connector 12. The braid 40, which can include from four to 64 braid wires, can be of flat or round stainless steel or polyamide based filament or other such suitable material and can be spiral or cross wound and varying from 10 to 100 picks or pitches per inch. The braid 40 imparts flexibility to the flexible microcatheter 10 while at the same time providing structure to preclude kinking or adverse bending or ovalization along the length of the flexible microcatheter 10, especially in the regions of reduced hardness (i.e., increased flexibility). The braid 40 also provides for structural integrity and for superior torque transmission qualities during rotation of the flexible microcatheter 10 during navigation and penetration of tortuous or other vascular paths. The outer layer 26 of resin, the attributes of which were described previously, is applied over and about and is formed to the braid 40 and inner layer 34, also comprised of resin, to form a one-piece composite catheter tube 16. Radio-opaque marker 44 can also be included at the distal end of the inner layer 34 in close proximity to the atraumatic tip 18 and a radio-opaque marker 42 can be located along the catheter shaft over the inner layer 34.

Figure 3:
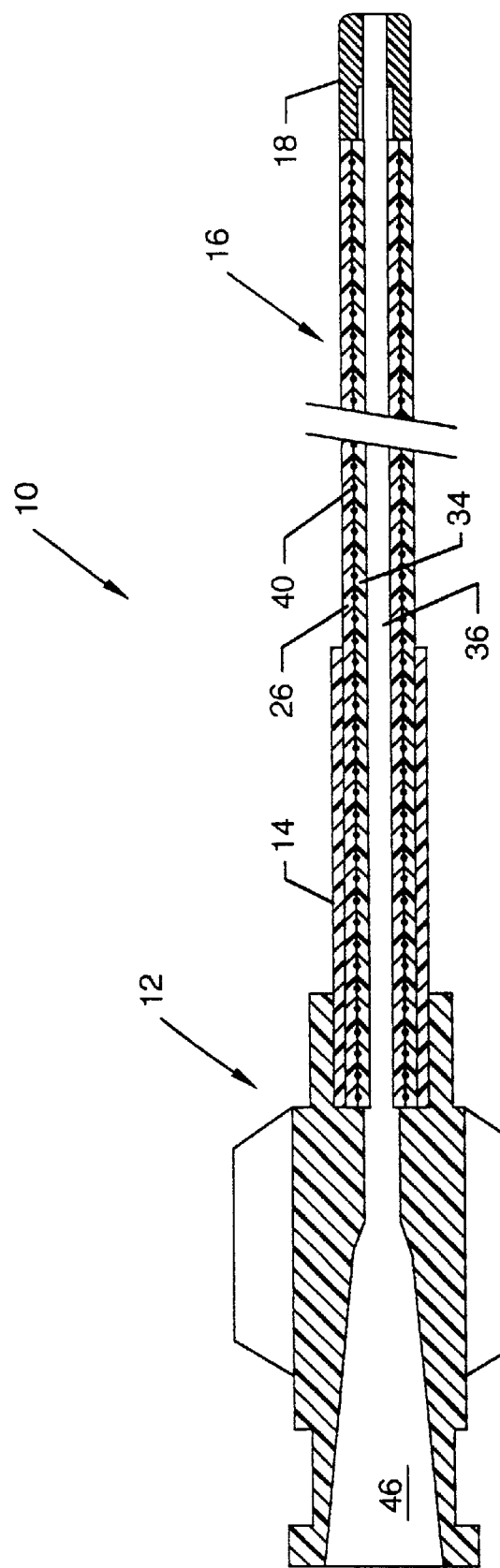

FIG. 3 illustrates a longitudinal cross sectional view of the flexible microcatheter 10, where all numerals correspond to those elements previously or otherwise described. Illustrated in particular are the outer and inner layers 26 and 34, respectively, having the braid 40 encapsulated therebetween to form the one-piece composite catheter tube 16. Also shown is the conically shaped cavity 46 located central to the Luer connector 12 which connects to the lumen 36 of the one-piece composite catheter tube 16. The operation of the microcatheter is based on the doctor's preference.

Various modifications can be made to the present invention without departing from the apparent scope hereof.

FLEXIBLE MICROCATHETER

PARTS LIST

- 10 flexible microcatheter
- 12 Luer connector
- 14 strain relief
- 16 one-piece composite catheter tube
- 18 atraumatic tip
- 20 distal region of flexibility
- 22 mid-region of flexibility
- 24 proximal region of flexibility
- 26 outer layer
- 28 resin, soft
- 30 resin, hard
- 32 resin, combo, medium
- 34 inner layer
- 36 lumen
- 38 resin, single
- 40 braid
- 42 radio-opaque marker
- 44 radio-opaque marker
- 46 conical cavity

What is claimed is:

1. A microcatheter comprising:
   a. a one-piece tubing formed of a polyether and polyamide copolymer, or a fluoroplastic inner layer;
   b. a braid of stainless steel wires over the inner layer to provide kink resistance or minimization of ovalization with bending and to increase torque transfer; and,
   c. an outer layer made up of a mixture of a polyamide base material, a polyether and polyamide base material, a polyurethane base material, one material having a 70–80 D Shore hardness value and the other material having a 25–35 D Shore hardness value; and wherein the amounts of the materials of said mixture forming said outer layer continuously vary along the length of said outer layer such that the hardness of said outer layer at a first point along the length of said outer layer is different than at any other point along the length of said outer layer, thereby attaining continuously variable stiffness of the microcatheter along its entire length.

2. A microcatheter comprising:
   a. a one-piece tubing formed of a polyether and polyamide copolymer, or a fluoroplastic inner layer;

b. a braid of stainless steel wires over the inner layer to provide kink resistance or minimization of ovalization with bending and to increase torque transfer; and, c. a continuously variable outer layer made up of a mixture or blend of a polyamide base material, a polyether and polyamide base material, or a polyurethane base material, one material having a 70–80 D Shore hardness value and the other material having a 25–35 D Shore hardness value, whereby the outer layer is continuously variable in flexibility and hardness over its length and has a distal end of said catheter of 25–35 D Shore hardness value, a transition region of the catheter increasing from 25–80 D Shore hardness value, and a proximal end is the catheter is 70–80 D Shore hardness value and wherein the amounts of the materials of said mixture forming said outer layer continuously vary along the length of said outer layer such that the hardness of said outer layer at a first point along the length of said outer layer is different than at any other point along the length of said outer layer, thereby attaining continuously variable stiffness of the microcatheter along its entire length.

3. The microcatheter of claim 2, wherein said continuously variable outer layer is produced by extrusion with a mixture or blend of the two materials of different hardness values being varied during the extrusion process, thereby attaining variable stiffness of the tubing along the length.

4. A microcatheter comprising:

a. a first section, a second section, and a third section, each of said sections including, in order, a continuous inner layer of constant composition extending through the first, second and third sections, a continuous braid extending through the first second and third sections, and a continuous outer layer made of a mixture two materials of different durometers and extending through the first, second and third sections;

b. said outer layer in said first section being about 100% soft durometer material;

c. said outer layer in said second section being continuously variable in durometer from about 100% soft to about 100% hard durometer material; and, d. said outer layer in said third section being about 100% hard durometer material and wherein the amounts of the two materials of said mixture forming said outer layer continuously vary along the length of said outer layer such that the hardness of said outer layer at a first point along the length of said outer layer is different than at any other point along the length of said outer layer, thereby attaining continuously variable stiffness of the microcatheter along its entire length.

5. A catheter comprising:

a. an elongated tubular means, with a first end and a second end, for passing material from said first end to said second end, said elongated tubular means including a single contiguous extrusion;

b. said single contiguous extrusion including at least two polymeric materials of differing elastic modulus, said polymeric materials being capable of processing to form a mixture with variable proportions of each polymeric material;

c. said polymeric materials being disposed along the length of said elongated tubular means to form a wall structure of said elongated tubular means;

d. said polymeric materials being combined as a mixture, with proportions varying along the length of said wall structure;

e. said varying proportions of said polymeric materials forming said wall structure and providing said wall structure with varying stiffness due to the variation in proportions of said polymeric materials of differing elastic modulus; and, f. said wall structure of varying stiffness providing said elongated tubular means with at least one region of relatively greater bending stiffness and at least one region of relatively lesser bending stiffness disposed at different distances relative to said first end and said second end along the length of said elongated tubular means;

and wherein the amounts of the two polymeric materials of said mixture forming said wall structure continuously vary along the length of said wall structure such that the hardness of said wall structure at a first point along the length of said wall structure is different than at any other point along the length of said wall structure, thereby attaining continuously variable stiffness of the catheter along its entire length.

6. The catheter of claim 5, further comprising:

a. a tubular polymeric inner layer;

b. a tubular middle layer comprising stiffening filament, disposed radially outside of and concentric with said inner layer;

c. said varying stiffness wall structure being disposed radially outside of and concentric with said middle layer; and, d. a hub disposed at said first end of said elongated tubular means, said hub providing for connection of said elongated tubular means to other devices and thereby providing for passage of material between the other devices and said elongated tubular means.

7. The catheter of claim 6, and further comprising a short atraumatic tip disposed at said second end of said elongated tubular means.

8. The catheter of claim 6, and further comprising a radio-opaque marking means.

9. The catheter of claim 5, wherein said elongated tubular means has a uniform inner diameter and a uniform outer diameter along its length between said first end and said second end.

10. The catheter of claim 5 comprising a region located between said first end and said second end of said elongated tubular means wherein said wall structure of varying stiffness has a gradual and continuous variation in stiffness along the length thereof, said gradual and continuous variation in stiffness being provided by a gradual and continuous variation in proportions of said polymeric materials.

11. The catheter of claim 5, wherein:

a. said wall structure of varying stiffness comprises an outer layer of said elongated tubular means;

b. a tubular braided metallic middle layer is disposed concentric with and radially inside and adjacent to said outer layer; and, c. a tubular polymeric inner layer is disposed concentric with and radially inside and adjacent to said outer layer.

* * * * *